United States Patent [19]

Haigh

[11] Patent Number: 4,806,469
[45] Date of Patent: Feb. 21, 1989

[54] PROCESS FOR THE DETERMINATION OF LIPASE ACTIVITY

[75] Inventor: Daniel H. Haigh, Sanford, Mich.

[73] Assignee: The Dow Chemical Company, Midland, Mich.

[21] Appl. No.: 714,140

[22] Filed: Mar. 20, 1985

Related U.S. Application Data

[63] Continuation-in-part of Ser. No. 420,453, Sep. 20, 1982, abandoned.

[51] Int. Cl.$^4$ ............................ C12Q 1/44; C12N 9/20
[52] U.S. Cl. ........................................ 435/19; 435/198; 436/71
[58] Field of Search ........................ 436/71, 85; 435/18, 435/19, 25, 134, 136, 147, 159, 183, 187, 198, 262, 288, 299; 528/491; 524/313; 526/329.1

[56] References Cited

U.S. PATENT DOCUMENTS

| | | | |
|---|---|---|---|
| 3,576,760 | 4/1971 | Gould et al. | 435/183 |
| 3,615,972 | 10/1971 | Morehouse et al. | 156/79 |
| 4,071,670 | 1/1978 | Vanzo et al. | 526/88 |
| 4,115,550 | 9/1978 | Fields et al. | 424/78 |
| 4,269,959 | 5/1981 | Lawton | 526/329.1 |
| 4,343,897 | 8/1982 | Neumann et al. | 435/19 |

FOREIGN PATENT DOCUMENTS 1319411  6/1973  United Kingdom.

OTHER PUBLICATIONS

Gaylord, N.G. et al, *Linear and Stereoregular Addition Polymers: Polymerization with Controlled Propogation* Interscience Publishers, Inc., New York, N.Y., p. 487 (1959).

*Primary Examiner*—Thomas G. Wiseman
*Assistant Examiner*—Charles L. Patterson, Jr.
*Attorney, Agent, or Firm*—Robert B. Ingraham; Thomas D. Zindrick

[57] ABSTRACT

Lipase activity is determined in an improved process for determining the activity thereof by providing a triglyceride imbibed or absorbed in a triglyceride swellable triglyceride insoluble polymer having a predetermined particle size.

15 Claims, 1 Drawing Sheet

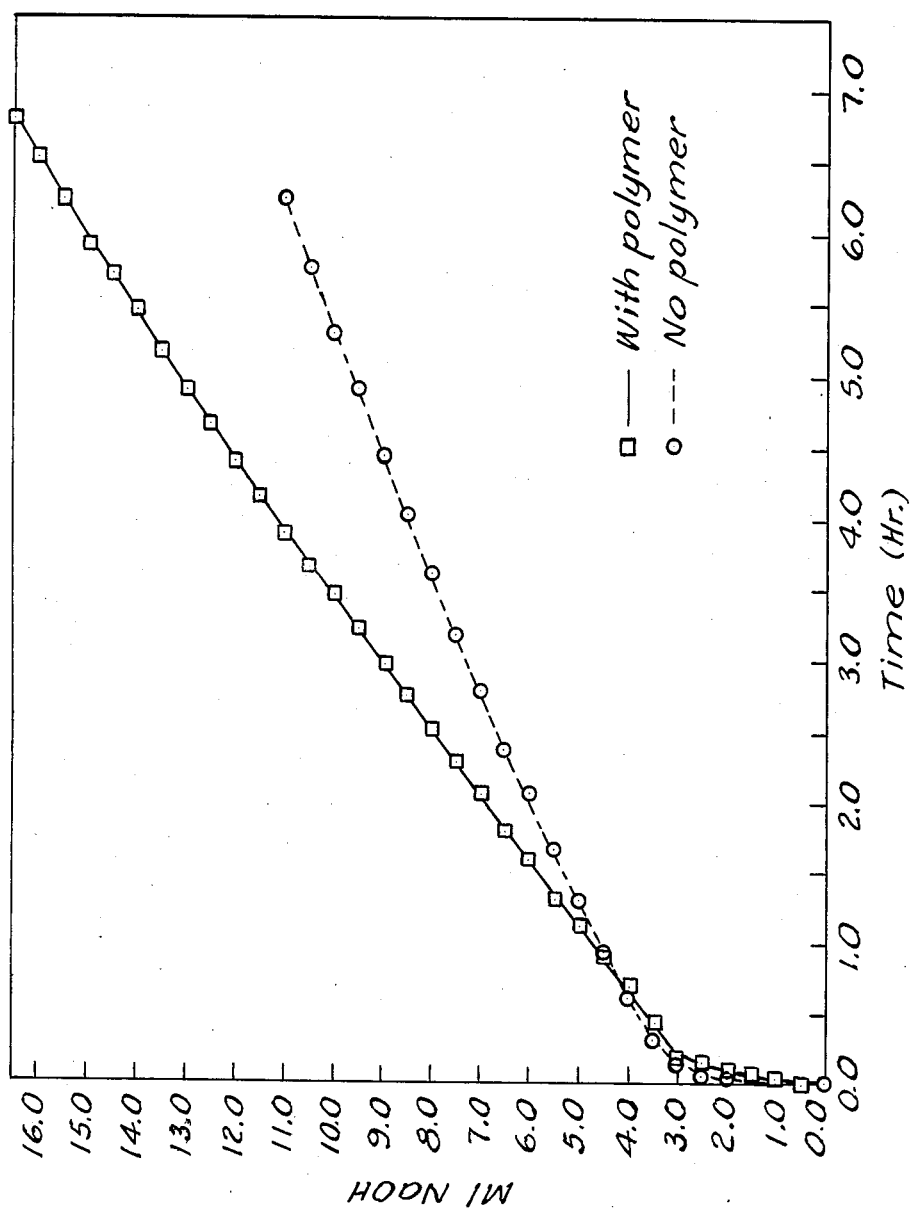

PROCESS FOR THE DETERMINATION OF LIPASE ACTIVITY

This application is a continuation-in-part of copending application Ser. No. 420,453, filed Sept. 20, 1982, now abandoned.

BACKGROUND OF THE INVENTION

In many clinical and hospital tests for the determination of duodenal or serum lipase activity, the lipase is admixed with a stabilized suspension of olive oil in an aqueous medium to present a triglyceride or triacylglycerol interface upon which the enzyme binds and accomplishes hydrolysis of the triglycerides. The efficiency of the lipase is then assessed by titration of the free fatty acid liberated during a specifc reaction period. Generally, a pH value of the aqueous dispersion is predetermined and when the pH is lowered to the predetermined value, a predetermined quantity of a dilute base is added to neutralize the fatty acids generated by the attack of the lipase on the triglyceride. A time versus volume of base plot provides a relative measure of the efficiency or activity of a given lipase. In assaying of this variety, particle size control is of great importance since the rate of reaction is dependent upon the surface area available to the lipase. If the triglyceride particles are relatively large, the hydrolysis rate will be relative low. Conversely, if the surface is relatively large, which is the case if the particles are very small, lipase hydrolysis rate will be relatively high. Thus, depending upon the stability of the triglyceride dispersions and their particle size, varying rates may be observed with no real difference in the activity of the lipase. Note Chemical Abstracts Volume 49; 12566d. The subject of hydrolysis at an oil/water interface is also discussed in Chemical Abstracts Volume 65; 2562g as well as Chemical Abstracts Volume 69; 41441n; Chemical Abstracts Volume 79; 144992t. Other attempts have been made to encapsulate enzymes such as that set forth in Chemical Abstracts Volume 73; 78221z and in Derwent Abstract 84877B/47.

Aqueous dispersions of triglycerides many times exhibit rather poor storage stability and exhibit a strong tendency to coalesce both in storage and during a test. Generally, such instability makes it difficult to determine the actual rate of lipolysis over any but the very early stages of hydrolysis of the triglycerides.

It would be desirable if there were available an improved method for the determination of lipase activity.

It would also be desirable if there were available an improved triglyceride dispersion which would provide a generally uniform surface area for a period of several hours.

It would also be desirable to have available an improved lipase activity test which would result in a more uniform evaluation of lipase activity.

SUMMARY OF THE INVENTION

These benefits and other advantages in accordance with the present invention are achieved in a process for the determination of lipase activity wherein a triglyceride is dispersed as a plurality of particles in an aqueous dispersion medium, a lipase is added to the aqueous dispersion medium, the lipase attacking the triglycerides and generating acyl acids, titrating the aqueous dispersion to determine the rate of generation of acyl acids, the improvement which comprises disposing the triglycerides within a plurality of particles of a triglyceride-swellable, triglyceride-insoluble synthetic resin prior to dispersing the triglycerides in the aqueous solution.

Discussion of the Preferred Embodiments of the Invention

The present invention can be practiced using any lipase and any triacylglycerol found in nature; for example, beef fat, olive oil, corn oil, cod liver oil and the like; or triglyceride mixtures either natural or synthetic.

The triglyceride-imbibing synthetic resins or polymers employed in the invention are solid and particulate including lightly crosslinked copolymers of, for example, isobornyl acrylate, isobornyl methacrylate, styrene or alkylstyrenes (preferably tertiary-alkylstyrenes wherein the alkyl groups contain from 4 to 12 carbon atoms) and one or more alkyl ester of a $C_1$ to $C_{20}$ alcohol and acrylic or methacrylic acid. The alkylstyrene can be, for example, 4-tert-butylstyrene, 4-tert-amylstyrene, 3,5-ditert-butylstyrene, 4-tert-hexyl-styrene, 4-tert-octylstyrene or 4-tert-dodecylstyrene. Tertiary-butylstyrene (4-tert-butylstyrene "TBS") is the preferred alkylstyrene. The alkyl ester monomers can include, for example, butyl methacrylate, butyl acrylate, hexyl acrylate, 2-ethylhexyl acrylate, cetyl methacrylate, eicosyl acrylate, the mixed ester cetyl-eicosyl methacrylate, lauryl methacrylate, stearyl methacrylate or lauryl acrylate. The alcohol moiety of the ester is preferably of 8 to 20 carbon atoms, and is preferably a linear fatty alcohol residue, such as cetyl, lauryl, stearyl or eicosyl, or a secondary alcohol residue. The alkylstyrene desirably, for ease of handling, should be the predominant monomer, the copolymer containing at least 50 percent by weight, and preferably from about 60 to about 85 to 90 percent by weight of the alkylstyrene. The alkyl ester monomer preferably includes both a methacrylate ester and an acrylate ester of one or more $C_8$ to $C_{20}$ fatty alcohols, or a $C_8$ to $C_{20}$ fatty alcohol methacrylate or acrylate as essentially the sole comonomer. The copolymer is preferably lightly crosslinked to insure that the polymer will not be soluble in or miscible with triglycerides. Too much crosslinking, i.e., one percent by weight or more, will hinder or prevent the polymer particles from imbibing fats. In general, the preferred polymers can contain from about 0.001 to about 0.1 percent by weight of a crosslinking agent (based on the total weight of the alkylstyrene and alkyl ester monomers). Preferably, about 0.01 to about 0.075 percent of crosslinking agent is employed. The crosslinking agent can be any di- or polyfunctional compound known to be useful as a crosslinking agent in polymeric vinyl addition compositions, such as divinylbenzene, vinyl isopropenyl benzene, butadiene, or other polyethylenically unsaturated crosslinking agents described, for example, in U.S. Pat. No. 3,520,806. Divinylbenzene is preferred as a crosslinking agent, in amounts from about 0.025 to about 0.05 to about 0.075 to about 0.1 weight percent.

The size of the polymer particles is related to the rate at which they absorb triglycerides. In general, for a given amount of polymer, the contact with triglycerides and the rate of triglyceride absorption is enhanced as the ratio of surface area to weight of the polymer increases. Thus, smaller particles, with diameters such as from 100–500 Angstrom units to 5 microns, generally imbibe triglycerides more rapidly than particles from 5 to 50 microns in diameter, which are, in turn, more rapid absorbers than particles in the 50 micron to 1 to 2 millimeter range.

Particles with an average diameter of about 60 to 100 microns or greater are difficult to maintain in aqueous suspension. Accordingly, particle sizes below about 50 microns are preferred, and preferably the particles are sufficiently small to form a stable aqueous dispersion.

In general, all the particles should be greater than about 1000 angstrom units wide at their smallest dimension. It is convenient to employ generally spherical particles which have diameters of from about 0.05 to about 50 microns. It is preferred to employ such particles with diameters from about 1 to about 60 microns.

The small particles can be prepared by a variety of known methods such as by emulsion or suspension polymerization techniques. Various techniques are disclosed in U.S. Pat. Nos. 3,615,972 and 4,071,670. Suspension polymerization is a well known process for forming polymer particles with spherical or bead-like configuration and relatively uniform particle size, and this technique can be conveniently employed to make the polymers.

The polymers are preferably, but not necessarily, prepared by emulsion or suspension polymerization of the monomers (and crosslinking agent) in an aqueous emulsion or aqueous suspension. In emulsion polymerization, the polymerization occurs in micelles formed by the monomer mixture and the emulsifier. In the suspension technique, polymerization occurs in monomer droplets suspended in the aqueous phase. Suspension polymerization is preferred for making larger particles, e.g., from about 0.3 to 0.5 micron and larger.

The polymerization reaction proceeds at temperatures from about 50° to 120° C., conveniently from 70° to 90° C., and in the presence of a minor amount (typically from about 0.5 to 10 times the amount of the crosslinking agent) of a polymerization initiator such as potassium persulfate or tertiary-butyl peroctoate. In preparing the copolymers, the monomers and crosslinking agent are mixed together, in the proportions corresponding to those desired for the product, then dispersed in water containing either an emulsifying agent or a suspending agent. The proportions are preferably selected as the monomer plus crosslinking agent comprises about 20 to about 60 percent by weight of the aqueous mixture. The polymerization initiator is mixed with either the monomer mixture or the aqueous phase depending on the polymerization method, the initiator used and its relative solubility in the two phases. The mixture is then mixed, e.g., with a high-shear mixer or a homogenizer, to disperse the monomer phase in the aqueous phase, and to reduce the particle size of the mixture of monomer and crosslinking agent to the size desired for suspension polymerization; and to form micelles of the desired size for emulsion polymerization. The resulting mixture is heated with stirring at a temperature in the polymerization temperature range until the reaction is substantially complete (generally 4 to 24 hours). The copolymer product can be recovered and worked up by conventional techniques such as filtration or screening to remove any coagulum or large-particle waste, dialysis, lyophilization or, particularly, with polymer particle sizes on the order of 0.15 micron and larger, by filtration to separate the reaction medium, alcohol precipitation, washing with lower alkanols, steam distillation or other known techniques.

In a convenient purification procedure for polymer particles prepared by suspension polymerization, the suspension is passed through a screen to remove any large coagulum waste particles, then mixed with about 10 parts by volume of isopropanol. The particles are allowed to settle, and the supernatant liquid removed by decantation. Washing with isopropanol can be repeated, if desired. The washed polymer particles can be separated by conventional techniques such as decantation, centrifugation, evaporation, or filtration. The washed particles can be used directly, or suspended in an aqueous carrier.

Purification is preferably achieved by isolating the material as a filter cake and then sequentially washing the intact filter cake with deionized water and then an alcohol such as, for example, 190 proof ethanol or isopropanol, under pressure.

The triglyceride swollen particles are readily obtained by contacting a body of particles with a quantity of triglyceride preferably sufficient to swell the particles to their maximum degree. The quantity of triglyceride to employ will depend upon the particular polymer particles used and their degree of crosslinking. The quantity is readily approximated by weighing an amount of imbibing polymer particles, applying a relatively low boiling hydrocarbon solvent to the beads; the solvent having solubility parameter approximating that of the triglyceride to be used, when the beads have reached an equilibrium of swelling, separating them from the nonimbibed hydrocarbon solvent and weighing the swollen beads. The volume of hydrocarbon which has been imbibed by the polymer particles can be readily calculated knowing the particle density. Knowing the density of the triglyceride the appropriate quantity to either fully swell the polymer particles or partially swell the polymer particles can be readily determined. Generally, for ease and convenience, the polymer particles may be separated by sieving or screening to provide a mass of particles of relatively narrow size distribution depending upon the needs of the particular person performing such a test. Generally, the particles may be dispersed in an aqueous medium with or without the aid of a dispersing agent, and with or without agitation. Generally, agitation is required only during titration.

By way of further illustration, a substrate was prepared employing a one to one by volume mixture of olive oil (Sigma Chemical Co., Product No. 0-1500) and a 5 weight percent aqueous gum arabic solution. The two aqueous solutions were sheared to a dispersion having a volume average diameter of about 20 microns.

A second substrate was prepared employing the same olive oil and lightly crosslinked polymer beads which were a polymer of about 70 weight percent tertiarybutylstyrene, about 30 weight percent lauryl methacrylate and about 0.05 weight percent divinylbenzene to provide particles of 24.7 micrometers volume average diameter. Four volumes of olive oil were shaken with one volume of the polymer beads until the olive oil was completely imbibed. 6.25 Grams of the olive oil polymer composite containing 5 grams of olive oil were taken with 5 milliliters of the 5 weight percent gum arabic aqueous solution. Each of the substrates so prepared was placed in a vessel with a nitrogen purge and 5 milliliters of 2 weight percent bile salts was added to the substrate and the pH was adjusted using 0.10 normal sodium hydroxide to 9.0. Subsequently 5 milliliters of an aqueous 0.3 weight percent type II lipase (Sigma Chemical Company porcine pancreatic enzyme; Sigma product No. L-3126) was added to induce hydrolysis. The results are set forth in the following FIGURE wherein each dot represents the addition of 0.5 milliliter of 0.10 normal sodium hydroxide when the pH of the respective solutions had reached a pH 8.5. The lower plot represents the substrate which did not employ the lightly crosslinked polymer beads, whereas the upper plot indicates the results obtained with the olive oil imbibed within the polymer beads. Note, a faster rate and more linear rate is obtained when using the method of the present invention when compared to the method of the prior art without the beads.

As is apparent from the foregoing specification, the present invention is susceptible of being embodied with various alterations and modifications which may differ particularly from those that have been described in the preceding specification and description. For this reason, it is to be fully understood that all of the foregoing is intended to be merely illustrative and is not to be construed or interpreted as being restrictive or otherwise limiting of the present invention, excepting as it is set forth and defined in the hereto-appended claims.

What is claimed is:

1. In a method for the determination of lipase activity wherein a triglyceride is dispersed as a plurality of particles in an aqueous dispersion medium, a lipase is added to the aqueous dispersion medium, the lipase attacking the triglyceride and generating acyl acids, and the aqueous dispersion is titrated to determine the rate of generation of acyl acids, the improvement which comprises disposing the triglyceride within a plurality of particles of a triglyceride-swellable, triglyceride-insoluble crosslinked synthetic resin prior to dispersing the triglyceride in the aqueous solution.

2. The method of claim 1 wherein the triglyceride is olive oil.

3. The method of claim 1 wherein the synthetic resin is a polymer of tertiary-butylstyrene.

4. The method of claim 1 wherein the synthetic resin is a polymer of tertiary-butylstyrene and a methylacrylate.

5. The method of claim 1 including the step of titrating the aqueous dispersion with sodium hydroxide.

6. The method of claim 1 wherein the particles prior to the addition of the triglyceride have a diameter of from about 100 angstroms to 2 millimeters.

7. The method of claim 1 wherein the particles prior to the addition of the triglyceride have a diameter of from about 0.5 to 50 microns.

8. The method of claim 1 wherein the particles prior to the addition of the triglyceride have a diameter of from about 1 to 60 microns.

9. The method of claim 1 including the step of screening the particles prior to disposing the triglyceride within the particles to obtain particles of generally like diameter.

10. The method of claim 1 including the step of adding a dispersion stabilizer to the aqueous dispersion medium.

11. The method of claim 10 werein the dispersion stabilizer is gum arabic.

12. The method of claim 1 wherein said process is carried out in a nitrogen atmosphere.

13. The method of claim 1 wherein the synthetic resin is a polymer of isobornylmethacrylate.

14. The method of claim 1 wherein the synthetic resin is a polymer of vinyltoluene.

15. The method of claim 1 wherein the synthetic resin is a polymer of styrene.

* * * * *